US006670116B2

(12) United States Patent
Zimmermann et al.

(10) Patent No.: US 6,670,116 B2
(45) Date of Patent: Dec. 30, 2003

(54) METHODS FOR THE DETECTION, QUANTIFICATION AND DIFFERENTIATION OF INFECTIOUS VERSUS NON-INFECTIOUS PATHOGENS IN A SAMPLE

(75) Inventors: Klaus Zimmermann, Vienna (AT); Dirk Völkel, Vienna (AT); Peter Turecek, Klosterneuburg (AT); Hans-Peter Schwarz, Vienna (AT); Manfred Rieger, Gänserndorf (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/745,017

(22) Filed: Dec. 20, 2000

(65) Prior Publication Data

US 2001/0034020 A1 Oct. 25, 2001

(30) Foreign Application Priority Data

Dec. 22, 1999 (AT) ............................... 2165/99

(51) Int. Cl.[7] ............................ C12Q 1/70; C12Q 1/68; C07H 21/02; C07H 21/04
(52) U.S. Cl. ............................ 435/5; 435/6; 435/91.2; 536/23.1; 536/24.3
(58) Field of Search ............................ 435/5, 6, 91.2; 536/23.1, 24.3

(56) References Cited

U.S. PATENT DOCUMENTS

| 4,683,195 A | 7/1987 | Mullis et al. |
| 4,683,202 A | 7/1987 | Mullis |
| 5,561,064 A | * 10/1996 | Marquet et al. |
| 5,789,153 A | 8/1998 | Falkner et al. ................ 435/5 |
| 5,858,658 A | 1/1999 | Haemmerle et al. |
| 2001/0053517 A1 | * 12/2001 | Anton et al. |

OTHER PUBLICATIONS

Vu et al., Nucleic Acids Research 28(7), e18, i–ix. (2000).*
Gupta et al., J. of Virology 71(8) : 6271–6275 (1997).*
Nogva et al., Applied and Environmental Microbiology 66(9): 4029–4036 (2000).
Sanyal et al., Molecular Biotechnology 8: 135–137 (1997).
Sheridan et al., Applied and Environmental Microbiology 64(4): 1313–1318 (1998).
Zimmermann et al., BioTechniques 21: 268–279 (1996).
Cabrerizo, M., et al., *Hepatitis B Virus DNA in Serum and Blood Cells of Hepatitis B Surface Antigen–Negative Hemodialysis Patients and Staff*, Journal of the American Society of Nephrology, pp. 1443–1447 (1997).

* cited by examiner

*Primary Examiner*—Ethan Whisenant
(74) *Attorney, Agent, or Firm*—Heller Ehrman White & McAuliffe

(57) ABSTRACT

Methods are disclosed that permit pathogenic agent detection and differentiation between infectious and non-infectious forms. Specifically, the present invention provides for pathogenic agent detection using nucleic acid amplification and detection techniques. Moreover, these nucleic acid amplification and detection techniques permit infectious pathogens to be distinguished from non-infectious forms. Also disclosed is a method used to detect and distinguishes between infectious and non-infectious pathogens in biological products and pharmaceutical preparations.

25 Claims, No Drawings

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
gccaagaaac cccgcattac c            21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
accagtttac catagtttga a            21

<210> SEQ ID NO 3
<211> LENGTH: 117
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gccaagaaac cccgcattac catgttatgg atagactggc taagcaaagc gcgatccaaa    60
acacaaaagg ctttgttcct tactctttaa actttgttca aactatggta aactggt      117

METHODS FOR THE DETECTION, QUANTIFICATION AND DIFFERENTIATION OF INFECTIOUS VERSUS NON-INFECTIOUS PATHOGENS IN A SAMPLE

CROSS REFERENCE TO RELATED APPLICATIONS

This application claims the benefit of Austrian patent application No. A2165/99, filed Dec. 22, 1999, which is herein incorporated by reference in its entirety.

FIELD OF THE INVENTION

The present invention related to methods for pathogenic agent detection, and differentiation between infectious and non-infectious forms. Specifically, the present invention relates to pathogen detection using nucleic acid amplification and detection techniques. Moreover, the present invention relates to nucleic acid amplification and detection techniques that permit infectious pathogens to be distinguished from non-infectious forms. More specifically, the preset invention relates to methods used to detect, and distinguishes between, infectious and non-infectious pathogens in biological products and pharmaceutical preparations.

BACKGROUND OF THE INVENTION

In is imperative that biological products intended for in vivo use be free of infectious pathogens. The use of biological products such as, but not limited to, those derived from human plasma are must be carefully tested for infectious pathogens before, during and after processing. The three methods most commonly employed to detect infectious pathogens are serological, cultures and nucleic acid detection assays. Serological methods are highly specific but lack sensitivity and cannot distinguish between living and non-living pathogens. Culturing methods only detect living pathogens and can be exquisitely sensitive if the pathogenic agent to be detected is easily cultivated. However, many pathogens such as hepatitis viruses and human parvovirus B19 cannot presently be cultured and other agents including the human immunodeficiency virus (HIV) are difficult to culture. Nucleic acid detection assays are highly sensitive and specific and can detect both cultivable and non-cultivable pathogens. Consequently, nucleic acid detection systems have become the method of choice for pathogenic agent detection.

Early nucleic acid detection assays used radioactive probes that hybridized with nucleic acid targets that had been extracted from the sample and captured on solid substrates such as filters or membranes. These systems, while extremely specific, lack sensitivity when target nucleic acid in a sample is scarce. However, nucleic acid detection sensitivity was dramatically improved in the late 1980's with the development of the polymerase chain reaction (PCR) assay and related nucleic acid amplification systems. Current nucleic acid amplification assays can detect as little as one copy of pathogen nucleic acid in a biological sample. Moreover, PCR assays have been adapted to automated platforms that permit the screening of hundreds of samples simultaneously. However, present nucleic acid assays, while highly sensitive and specific, cannot distinguish between living and non-living pathogen.

Many biological products are prepared from human plasma sources. These human plasma sources are initially screened for the presence of pathogens using nucleic acid detection systems including PCR. Samples that test negative for selected pathogens are then pooled and processed. Processing steps generally involve pathogen inactivation methods designed to eliminate residual infectious risk should an infectious agent detection assay fail to identify a contaminated sample. Pathogens that present the greatest concern to biological product manufactures are generally viral pathogens, such as, but not limited to hepatitis a virus (HAV), hepatitis B virus (HBV), hepatitis C virus (HCV), human parvovirus B19 (B19), transfusion transmissible virus (TTV), and human retroviruses including HIV, human lymphotropic virus types I and II (HTLV I and HTLV II). Biological product manufactures have developed validated viral inactivation techniques for these agents. Consequently, the risk of transmitting one or more of these agents in a biological product is extremely remote.

Moreover, processed biological materials are tested using nucleic acid detection techniques at various manufacturing stages and again after the final product has been formulated and packaged. On extremely rare occasions pathogen derived nucleic acids (target nucleic acid) may be detected in the final product. The contamination may have come from product supplements such as albumin or may have been missed during initial screening. In some cases, product processing steps may include extraction and concentration procedures that make previously undetectable target nucleic acids detectable. When target nucleic acid is detected in a finished product, the product is generally destroyed. However, in most cases the product would have been entirely safe for its intended use because the target nucleic acid detected was from an inactive, or killed pathogen.

Furthermore, final products derived using recombinant DNA technology intended to replace biological products derived from high risk starting materials may also be contaminated with detectable target nucleic acids. Present regulatory guidelines require that these recombinant DNA technology based biological (recombinant biologicals) must be destroyed even though the contaminate has generally come from product supplements such as albumin that has been subjected to infectious pathogen inactivation processes. Many biological products are extremely scarce and must be derived from plasma sources that present a risk of having transmissible pathogens present. Consequently, the raw materials needed to make many products are in short supply and the costs associated with destroying other wise perfectly safe an effective biologicals is high and can result in shortages of essential therapeutic agents.

Therefore, a pathogenic agent detection assay that combines the sensitivity and specificity of PCR with the ability to discriminate between infectious and non-infectious pathogens would represent a significant advance to biological product development and production.

BRIEF SUMMARY OF THE INVENTION

The present invention provided a solution to this and other problems associated with current nucleic acid detection assays. In one embodiment of the present invention a method is provided wherein a sample is tested using PCR and the total amount of target nucleic acid present is quantified. Next the sample, or an aliquot therefrom, is treated with one or more enzymes that cleaves free nucleic acids and then total target nucleic acid is quantified a second time using PCR. The total amount of target nucleic acid detected in the treated sample or aliquot is compared to the amount present prior to enzyme treatment. Unprotected target nucleic acid present in the sample will be destroyed by the nucleic acid-cleaving enzymes rendering them undetectable using PCR. Unprotected target nucleic acids present in the sample represent nucleic acids remaining after pathogen inactivation procedures have killed the pathogen.

Infectious pathogens, specifically viral pathogens, package their nucleic acids within a protein or protein/lipid/glycolipid structure referred to as a capsid. The viral capsid protects the viral nucleic acid (encapsulated nucleic acids) from nucleic-acid cleaving enzymes such as nucleases including, but not limited to RNase and DNase. However, many viral inactivation protocols effectively kill virus by destroying the integrity of the capsid rendering their nucleic acid susceptible to nuclease digestion. The present invention provides methods that differentiate between protected viral nucleic acid and viral nucleic acids susceptible to nuclease attack. A sample is deemed to have non-infectious viral contamination when nucleic acid detection levels are substantially or completely diminished following nuclease treatment as compared to the untreated sample.

Generally, in one embodiment of the present invention a method for detection, differentiation and quantification of free and encapsulated target nucleic acids in a sample consists of determining a first total target nucleic acid content in the sample (un-digested sample). Next a nuclease is added to the sample to digest free target acids in the sample to form a digested sample. After digestion is complete, the total remaining target nucleic acid content of the digested sample (free target nucleic acid) is determined and quantified. Quantification is accomplished by subtraction of the target nucleic acid content in the digested sample from the first determined target nucleic acid content in the un-digested sample. It is understood to those having ordinary skill in the art that the entire sample can be tested, or individual aliquots can be removed and tested separately. Moreover, if individual aliquots are used, the order in which the methods of the present invention is conducted is not important. It is envisioned that all variations in sample aliquots and assay sequence steps considered encompassed by the teachings of the present invention.

By treatment with a nucleic acid-cleaving enzyme according to the invention, only those nucleic acids that are not protected by a protein envelope are digested. Accordingly, only those nucleic acids that were protected by a protein envelope before digested during enzyme treatment are detected in the nucleic acid amplification that follows enzyme treatment. Consequently, during enzymatic digestion, all the nucleic acids that originate from actually inactivated viruses are removed (whose protein envelope, for example, burst, or whose DNA became accessible to the enzyme because of inactivation treatment). The nucleic acid that is still situated in intact viruses (and therefore still potentially infectious) cannot be attacked by the nucleic acid-cleaving enzyme; the nucleic acid remains intact and can be detected in a nucleic acid amplification method that follows enzymatic digestion.

The method according to the invention is therefore also excellently suited for determination and control of the virus inactivation rate of a virus inactivation step using a nucleic acid amplification method. Therefore, in another embodiment of the present invention a known concentration of a target virus to be inactivated is added to a sample. An inactivation process is then conducted to inactivate the target virus followed by determining a first total of target virus nucleic acid content in the sample. Then a nuclease is added to the sample to digest free target virus nucleic acids and form a digested sample. Next the total target virus nucleic acid content in the digested sample is quantified and the total amount of free target virus nucleic acid in the sample is determined. Total free target nucleic acid is determined by subtracting the target virus nucleic acid content in the digested sample from the target virus nucleic acid content in the un-digested sample. Here again, specific aliquots can be removed or the entire sample subjected to the method according to the invention.

The method according to the invention is preferably employed in the production of pharmaceutical preparations that start from a starting material that can potentially contain human pathogenic viruses. Such preparations must be subjected to the most demanding quality assurance with respect to virus load, for example, by control with nucleic acid amplification methods. It is then also essential to provide one or more steps for inactivation or depletion of any viruses that may be present in the sample. However, it is essential that any assay used to detect viral pathogens in a sample also be capable of distinguishing between infectious and non-infectious forms.

The present invention therefore also concerns a method for production of a pharmaceutical preparation subjected to quality assurance with respect to the load of specific viruses, starting from an initial material that is potentially burdened with viruses, which includes, in addition to the usual production steps for the specific preparation, the process included the teachings of the present invention. For example, after the pharmaceutical preparation has been processed, an infectious (target) virus inactivation procedure is performed on the sample. Next a first total of target virus nucleic acid content in the sample is determined. Then a nuclease is added to the sample to digest free target virus nucleic acids forming a digested sample. Next the total target virus nucleic acid content in the digested sample is quantified and the total amount of free target virus nucleic acid in the sample is determined. Total free target nucleic acid is determined by subtracting the target virus nucleic acid content in the digested sample from the target virus nucleic acid content in the un-digested sample. Here again, specific aliquots can be removed or the entire sample subjected to the method according to the invention. By using the teachings of the present invention pharmaceutical preparations containing non-infectious viral nucleic acids will not be confused with potentially infectious preparations and destroyed.

In similar fashion the method according to the invention can also be used for control and quality assurance of production of a pharmaceutical preparation subjected to quality assurance with respect to load of specific viruses, starting from an initial material that can potentially be loaded with viruses, in which the production method or one or more steps of the production method are controlled with the measures according to the invention, advantageously removing aliquots from the different processing stages.

In another embodiment the present invention can be used to validate infectious pathogen inactivation protocols for biological products. A known dose of infectious pathogen is added to a (spiked) infectious pathogen-free biological sample. After the biological sample has been spiked with the infectious pathogen a nucleic acid detection assay, preferably PCR, may be performed to confirm that the sample had been spiked. Moreover, this preliminary PCR assay also serves to quantify the amount of infectious pathogen detectable in the sample. After the sample has been spiked and any preliminary PCR assays have been performed, the sample is subjected to an infectious pathogen inactivation protocol.

The inactivated biological sample is tested again to determine the total amount of infectious pathogen (target) nucleic acid in the post inactivation sample. Then a nuclease is added to the sample to digest free target virus nucleic acids forming a digested sample. Next the total target virus nucleic acid content in the digested sample is quantified and the total amount of free target virus nucleic acid in the sample is determined. Total free target nucleic acid is determined by subtracting the target virus nucleic acid content in the digested sample from the target virus nucleic acid content in the un-digested sample. An un-digested spiked sample may be run in parallel as a nuclease digestion control.

An infectious agent inactivation protocol is considered validated when the total amount of target nucleic acid in the post inactivated, un-digested sample is reduced to undetectable quantities after nuclease digestion. Here again, specific aliquots can be removed or the entire sample subjected to the method according to the invention.

The nucleic acid-cleaving enzyme is chosen according to the nucleic acid being detected or determined, and preferably DNases and RNases are used according to the invention. Free DNA or RNA molecules can be quantitatively digested with these enzymes so that such molecules can no longer be detected in large part in a nucleic acid amplification method. However, it is naturally also possible to use more specific enzymes, like restriction endonucleases. However, the nucleic acid amplification method then must be adjusted to the special cleavage site which is recognized by the restriction endonuclease, in which the cleavage site lies in the amplified region, for example.

The fact that the DNA of inactive HBV particles in the serum of patients can in principle be degraded in such a method was described by Cabrerizo et al. (J. Am. Soc. Nephrology 8 (1997):1443–1447); the modified and specially adapted application of DNase treatment for detection, differentiation and quantification of contaminating nucleic acid or for control of the inactivation rate or of a production process for biological drugs, however, has thus far not been considered, despite the enormous demand.

The present method is suitable not only for biological drugs from blood or plasma, but also for all recombinant products recovered from cell lines. Such cell lines can also yield potentially virus-loaded material in whose processing the method according to the invention can be efficiently used. The method according to the invention is generally applicable anywhere a differentiation must be made between the two forms of viral nucleic acid-free and encapsulated.

A possibility was also created with the present process of differentiating between free and encapsulated forms of viruses in which no infectious test at all has thus far been available or in which such tests are costly or very slow. The method according to the invention is orders of magnitude faster than ordinary cell culture tests.

In the method according to the invention, standard nucleic acids are preferably added to the sample or the starting material or aliquots removed from it before nucleic acid amplification and the performance of the nucleic acid amplification method controlled according to U.S. Pat. No. (USPN) 5,789,153 issued Aug. 8, 1998 to Falkner et al.

The standard nucleic acids are preferably added before treatment with the nucleic acid-cleaving enzyme, since the effectiveness of enzyme treatment can then also be controlled. In order to be able to also control the nucleic acid amplification method following enzyme treatment, the standard nucleic acids are preferably also added after enzyme treatment. Optimally, a standard nucleic acid is added both before the first nucleic acid amplification and also right before the second nucleic acid amplification, in which the standard nucleic acids added at the different times also differ from each other, for example, with respect to their length. Control with an internal standard is preferably carried out with the method described in U.S. Pat. No. 5,858,658 on Jan. 12, 1999 to Falkner etal. An internal control of the method, however, is also possible by adding model viruses, e.g., Sindbis, VSV or bacteriophages.

The special embodiment of nucleic acid amplification that is chosen is guided primarily according to the nature of the nucleic acid being detected, and preferably reverse transcriptase PCR (RT-PCR) or PCR is carried out in U.S. Pat. Nos. 4,683,202 and 4,683,195 both issued Jul. 28, 1987 to Mullis.

Because the nucleic acid-cleaving enzyme can have an interfering effect during subsequent nucleic acid amplification or subsequent processing steps, it is preferably inactivated or separated right after enzyme treatment. A preliminary purification of the samples can optionally also be carried out before enzyme treatments so that enzyme digestion and subsequent nucleic acid amplification are no longer influenced by interfering substances. Preliminary purification with microcolumns is then particularly preferred, for example, the centrifugation filter Microcon® YM100 (Millipore) or equivalent products with simultaneous buffering, e.g., in PBS.

The invention is further explained by reference to the following non-limiting examples.

DETAILED DESCRIPTION OF THE INVENTION

EXAMPLE 1

Differentiation Between Free and Encapsulated Parvovirus B19 Nucleic Acid After Incubation of the Viruses at Different Temperatures In this example infectious parvovirus B19 virus was incubated 10 minutes per charge with a copy number of approximately 10,000 in 10 $\mu$L PBS (i.e., in a physiological buffer solution that does not destroy the virus sheath) at different temperatures. The temperatures were 37, 50, 60, 80 and 99° C. The sample was then cooled again and a charge removed as control sample (undigested). After addition of 1 $\mu$L 50 mM MgCl$_2$ buffer and 1 $\mu$L DNase (Roche, Mannheim, Germany corresponding to 10 U), the remaining charges were incubated for 1 h at 37° C. The DNase activity was destroyed without residue by incubation at 99° C. The samples were then used directly for PCR. For quantitative checking of the digestion that occurred, single-strand oligonucleotides were used as the internal standard in different concentrations from 10 to 10,000 copies. The PCR solution of a total of 50 $\mu$L contains 1 Units of HotStarTaq™ (Qiagen, Hilden, Germany) in addition to the sample, the buffer of the manufacturer according to information, 200 $\mu$M of each dNTP and 50 pmol of each of the primers KK5, SEQ ID NO: 1 and KK6 SEQ ID NO: 2 (see Table 1 for sequences of primers and standard). The samples were layered with 50 $\mu$L mineral oil and initially incubated for 14 minutes at 94° C. for activation of polymerase. Forty-five cycles were then amplified according to the following profile in a TRIO thermounit (Biometra, Göttingen, Germany): 30 sec at 94° C., 30 sec at 55° C., 60 sec at 72° C. with a final elongation step at 72° C. for 1 min. 8 $\mu$L of the charge was applied to a 3.5% low-melting agarose gel. The result of the experiment is shown in Table 2. The copy number was only determined semi-quantitatively. It was found that, in comparison with the control (i.e., about 10,000 viruses which were directly used for PCR), the samples that were only incubated but not treated with DNase yielded the same copy numbers quite accurately. With increasing temperature the number of free nucleic acids increases, which means that the copy numbers determined diminishes after DNase treatment.

The experiment also shows that viruses that were not extracted beforehand can also be directly used in PCR. A comparison with the corresponding amount of extracted viruses gave the same copy numbers for the encapsulated nucleic acids of parvovirus B19.

TABLE I

Sequences of the oligonucleotides and primers employed

SEQ ID NO: 1 KK5 5'-GCCAAGAAACCCCGCATTACC-3'
SEQ ID NO: 2 KK6 5'-ACCAGTVTACCATAGTTTGAA-3'
SEQ ID NO: 3 B19c 5'-GCCAAGAAACCCCGCA1TACCATGTTATGGATAGACTGGC
TAAGCAAAGCGCGATCCAAAACACAAAAGGCTTTGTTCCT
TACTCTTTAAACTTTGTTCAAACTATGGTAAACTGGT-3'

TABLE 2

Effect of temperature on release of nucleic acids from virus particles.

| Temperature | Control | DNA Digestion |
|---|---|---|
| 37° C. | 10 000 | 5000 |
| 50° C. | 10 000 | 500 |
| 60° C. | 10 000 | 50 |
| 80° C. | 10 000 | 10 |
| 99° C. | 10 000 | 10 |

The data refer to the approximate copy numbers of B19 after incubation at different temperatures and after subsequent DNase digestion.
Control: Sample not digested with DNase.

EXAMPLE 2

Differentiation Between Free And Encapsulated Viruses in Biological Products

In this example two blood products in the final containers, FVIII and FIX, were investigated with reference to their content of free nucleic acids. For this purpose, 200 µL of the corresponding product was made up to 0.5 mL with PBS, introduced to Microcon YM100 columns and centrifuged at full speed. The columns were then refilled with PBS and the procedure repeated until a purification factor of at least 10 was attained. The sample was investigated, on the one hand, for content of parvovirus B19 nucleic acids undigested after the aforementioned method and, on the other hand, after DNase treatment. Table 3 shows the differentiation between the B19 copy number after DNA digestion (+DNase) and free nucleic acids with DNase (−DNase) for both products (two examples each).

TABLE 3

| | Without DNase | With DNase |
|---|---|---|
| FVIII (a) | 5000 | 20 |
| FVIII (b) | 6000 | 50 |
| FIX (a) | 300 | <10 |
| FIX (b) | 20000 | 50 |

It could be clearly demonstrated that the largest part of the B19 copy numbers determined were attributed to free DNA. No exact assertions can be made concerning the remaining B19 copy numbers (after DNase digestion). These viruses are presumably no longer infectious, for example, the sheath of the viruses could have been altered. On the other hand, the DNase digestion could also not have occurred 100%.

EXAMPLE 3

Efficiency of DNase Digestion

It can be gathered from the previous examples that the DNase treatment does not always lead to complete digestion of the freely occurring DNA molecules. Since no pre-purified DNA can be used for the experiments, one of the reasons can be that substances present in the solution hamper DNase digestion. On the other hand, not all DNA molecules could be freely accessible to digestion, for example, by mutual accumulation. Already inactive DNase molecules could also be added to the DNA and therefore hamper digestion. It was therefore investigated up to which copy numbers of a specific nucleic acid complete digestion could be achieved under optimal conditions.

For this purpose ca. 300, 1000, 3000 and 10,000 copies of a parvovirus B19 DNA were treated as described above in corresponding buffers (i.e., without inhibiting substances) with DNase and amplified with PCR. As is apparent in Table 4, 300 and 1000 copies were still readily digestible, whereas 3000 copies led to a weak band and 10,000 copies to a strong band.

This means if one intends to digest 3000 or more copies of a nucleic acid, the DNase digestion should be repeated or combined with digestion by restriction enzymes in order to obtain a reliable result even with such high copy numbers.

TABLE 4

Efficiency of DNase digestion

| B19 Copy Numbers | PCR-Signal |
|---|---|
| 300 | − |
| 1000 | − |
| 3000 | + |
| 10 000 | ++ |

Reference has been made herein to various patents, printed publications and manufacture instructions for use. Each of the aforementioned references is incorporated herein by reference in their entirety.

What is claimed is:

1. A method far determining the type of target nucleic acids in a sample, wherein the method is capable of differentiating free and encapsulated target nucleic acids in the sample, wherein the method comprises
   (a) determining a total target nucleic acid content in the sample;
   (b) adding a nuolease to the sample to digest free target nucleic acids in the sample to form a nuclease-treated sample;
   (c) determining a total target nucleic acid content remaining in the nuctease-treated sample, thereby quantifying the amount of encapsulated target nucleic acids in the sample; and
   (d) quantifying the total amount of free target nucleic acid in the sample by subtracting the determined amount of target nucleic acid content in the nuclease-treated sample from the determined amount of total target nucleic acid content in the sample, wherein steps (c) and (d) determine the types of target nucleic acids in the sample; differentiating free and encapsulated target nucleic acids in the sample, wherein the method comprises
   (a) determining a total target nucleic acid content in the sample;
   (b) adding a nuclease to the sample to digest free target nucleic acids in the sample to form a nuclease-treated, wherein the nuclease will not digest the encapsulated target nucleic acids;
   (c) determining a total target nucleic acid content remaining undigested in the nuclease-treated sample, which represents the amount of infectious pathogens in the sample;
   (d) quantifying the total amount of free target nucleic acid in the sample by subtracting the determined amount of undigested target nucleic acid content in the nuclease-treated sample from the determined amount of total target nucleic acid content in the sample, wherein the quantifying indicates the amount of inactivated pathogens in the sample; and
   (e) comparing the amounts from steps (c) and (d) to determine the proportion of infectious pathogens and inactivated pathogens in the sample.

2. The method of claim 1 wherein the nucleic acid amplification assay is a polymerase chain reaction (PCR) assay or a reverse transcriptase (RT) PCR assay.

3. The method of claim 1, further comprising adding a nucleic acid standard to the sample before the total target nucleic acid content of (a) is determined.

4. The method of claim 1, further comprising adding a nucleic acid standard to the sample after the free target nucleic acids in the sample are digested with the nuclease.

5. The method of claim 1, the nuclease is inactivated after the free nucleic acids in the sample are digested.

6. The method of claim 1, wherein the nuclease is a DNase or an RNase.

7. The method of claim 1, wherein the sample is selected from the group consisting of blood, plasma, serum, cell culture fluids, cells and a pharmaceutical preparation.

8. A method for determining the proportions of infectious pathogens and inactivated pathogens in a sample, wherein the method is capable of differentiating free and encapsulated target nucleic acids in the sample, wherein the method comprises
   (a) determining a total target nucleic acid content in the sample;
   (b) adding a nuclease to the sample to digest free target nucleic acids in the sample to form a digested sample, wherein the nuclease will not digest the encapsulated target nucleic acids;
   (c) determining a total target nucleic acid content remaining in the digested sample, which represents the amount of infectious pathogens in the sample;
   (d) quantifying the total amount of free target nucleic acid in the sample by subtracting the determined amount of target nucleic acid content in the digested sample from the determined amount of total target nucleic acid content in the sample, wherein the quantifying indicates the amount of inactivated pathogens in the sample.

9. The method of claim 8, wherein the nucleic acid amplification assay is a polymerase chain reaction (PCR) assay or a reverse transcriptase (RT) PCR assay.

10. The method of claim 8, further comprising adding a nucleic acid standard to the sample before the total target nucleic acid content of (a) is determined.

11. The method of claim 8, further comprising adding a nucleic acid standard to the sample after the free target nucleic acids in the sample are digested with the nuclease.

12. The method of claim 8, wherein the nuclease is inactivated after the free nucleic acids in the sample are digested.

13. The method of claim 8, wherein the nuclease is a DNase or an RNase.

14. The method of claim 8, wherein the sample is selected from the group consisting of blood, plasma, serum, cell culture fluids, cells and a pharmaceutical preparation.

15. The method according to claim 8, wherein the pathogen is a virus.

16. The method according to claim 15, wherein the virus is selected from the group consisting of parvovirus, hepatitis virus and human immunodeficiency virus.

17. A method for detecting infectious pathogens in a sample, wherein the method comprises
   (a) determining a total target nucleic acid content in the sample;
   (b) adding a maclease to the sample to digest any free target nucleic acids in the sample to form a digested sample, wherein the nuclease will not digest the encapsulated target nucleic acids; and
   (c) determining a total target nucleic acid content remaining in the digested sample, which represents the amount of infectious pathogens in the sample.

18. The method of claim 17, wherein the nucleic acid amplification assay is a polymerase chain reaction (PCR) assay or a reverse transcriptase (RT) PCR assay.

19. The method of claim 17, further comprising adding a nucleic acid standard to the sample before the total target nucleic acid content of (a) is determined.

20. The method of claim 17, further comprising adding a nucleic acid standard to the sample after the free target nucleic acids in the sample are digested with the nuclease.

21. The method of claim 17, wherein the nuclease is inactivated after the free nucleic acids in the sample are digested.

22. The method of claim 17, wherein the nuclease is a DNase or an RNase.

23. The method of claim 17, wherein the sample is selected from the group consisting of blood, plasma, serum, cell culture fluids, cells and a pharmaceutical preparation.

24. The method according to claim 17, wherein the pathogen is a virus.

25. The method according to claim 24, wherein the virus is selected from the group consisting of parvovirus, hepatitis virus and human immunodeficiency virus.

* * * * *